(12) United States Patent
Patil (10) Patent No.: US 10,231,979 B2
(45) Date of Patent: Mar. 19, 2019

(54) MODULATION OF INFLAMMATION USING PROGESTERONE METABOLITES

(71) Applicant: Indiana University Research and Technology Corporation, Indianapolis, IN (US)

(72) Inventor: Avinash Shivaputrappa Patil, Zionsville, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 166 days.

(21) Appl. No.: 15/229,793

(22) Filed: Aug. 5, 2016

(65) Prior Publication Data

US 2017/0035782 A1  Feb. 9, 2017

Related U.S. Application Data

(60) Provisional application No. 62/202,461, filed on Aug. 7, 2015.

(51) Int. Cl.
| | | |
|---|---|---|
| *A61K 31/57* | (2006.01) | |
| *A61P 43/00* | (2006.01) | |
| *G01N 33/74* | (2006.01) | |

(52) U.S. Cl.
CPC ............ *A61K 31/57* (2013.01); *A61P 43/00* (2018.01); *G01N 33/743* (2013.01); *G01N 2800/368* (2013.01); *G01N 2800/50* (2013.01)

(58) Field of Classification Search
CPC ............. A61K 31/122; A61K 31/57; G01N 2800/368; G01N 2800/50; G01N 33/743
USPC .......................................... 514/691, 1, 454
See application file for complete search history.

(56) References Cited

U.S. PATENT DOCUMENTS

| | | | | |
|---|---|---|---|---|
| 4,201,778 A | * | 5/1980 | Draper ................. | C07J 5/0076 514/179 |
| 7,884,093 B2 | * | 2/2011 | Creasy ................. | A61K 31/57 514/177 |
| 8,614,203 B2 | * | 12/2013 | Stein ................... | A61K 31/57 514/177 |
| 2013/0023505 A1 | * | 1/2013 | Garfield ............... | A61K 31/57 514/178 |

FOREIGN PATENT DOCUMENTS

WO  WO-2015161078 A1 * 10/2015 ........... G01N 33/574

OTHER PUBLICATIONS

Amaral et al., Hypertension, Jan. 2015, vol. 65, Issue 1, p. 225-231.*
Lyttle et al., Am J Obstet Gynecol. Sep. 2009; 201(3):284.e1-284.e7.*
Kanceva, Physiol. Res. 64 (Suppl. 1): S247-S254, 2015.*
Perry, Semin Immunopathol (2013) 35:601-612.*
Nold et al., "Prevention of preterm birth by progestational agents: what are the molecular mechanisms?", Mar. 2013, Am. J. Obstet. Gynecol., 208(3), pp. 223.e1-223.e7. (Year: 2013).*
Kiprono et al., "Progesterone blunts vascular endothelial cell secretion of endothelin-1 in response to placental ischemia", Jul. 2013, Am. J. Obstet. Gynecol., 209(1), pp. 44.e1-44.e6. (Year: 2013).*
Amaral et al., "Progesterone supplementation attenuates hypertension and the autoantibody to the angiotensin II type I receptor in response to elevated interleukin-6 during pregnancy", Aug. 2014, Am. J. Obstet. Gynecol., 211(2), pp. 158.e1-158.e6. (Year: 2014).*
Patil et al., "Fetal metabolism of progesterone: effect of proposed metabolites on uterine contractility", Jan. 2014, Am. J. Obstet. Gynecol., 210(1), Supplement, S355. (Year: 2014).*
Patil et al., "Progesterone metabolites modulate uterine smooth muscle inflammation", Dec. 2015, Am. J. Obstet. Gynecol., 213(6), p. 887. (Year: 2015).*

* cited by examiner

*Primary Examiner* — My-Chau T. Tran
(74) *Attorney, Agent, or Firm* — Stinson Leonard Street LLP (57) ABSTRACT

Methods for modulating inflammation using progesterone metabolites are disclosed. More particularly, methods of administering progesterone metabolites, 6β-hydroxyprogesterone (6β-OHP) and 16α-hydroxyprogesterone (16α-OHP) are disclosed for mitigating inflammation in various tissue types in the body.

5 Claims, 10 Drawing Sheets
(2 of 10 Drawing Sheet(s) Filed in Color)

MODULATION OF INFLAMMATION USING PROGESTERONE METABOLITES

CROSS REFERENCE TO RELATED APPLICATIONS

This application claims priority under 35 USC § 119(e) to U.S. Provisional Application Ser. No. 62/202,461 filed on Aug. 7, 2015, the entire disclosure of which is incorporated herein by reference.

BACKGROUND OF THE DISCLOSURE

The present disclosure relates generally to modulating inflammation using progesterone metabolites. More particularly, the present disclosure relates the use of two progesterone metabolites, 6β-hydroxyprogesterone (6β-OHP) and 16α-hydroxyprogesterone (16α-OHP), for mitigating inflammation in various tissue types in the body. In one particularly suitable embodiment, the metabolites modulate uterine contractility in patients with localized uterine inflammation/infection. In another suitable embodiment, the metabolites mitigate systemic inflammation though their effects on monocytes and macrophage differentiation/function.

Inflammation is a process by which tissues respond to various insults. It is characterized by upregulation of chemokines, cytokines, and pattern recognition receptors that sense microbes and tissue breakdown products. During pregnancy, the balance of Th1 (cell-mediated immunity) and Th2 (humoral immunity) cytokines is characterized by an initial prevalence of Th2 cytokines, followed by a progressive shift toward Th1 predominance late in gestation, that, when is abnormal, may initiate and intensify the cascade of inflammatory cytokine production involved in adverse pregnancy outcomes. Maternal and placental hormones may affect the inflammatory pathway. Hypoxia and the innate immune response are 2 adaptive mechanisms by which organisms respond to perturbation in organ function, playing a major role in spontaneous abortion, intrauterine growth restriction, preeclampsia, and preterm delivery.

Preterm labor is defined as the presence of uterine contractions of sufficient frequency and intensity (also referred to herein as contractile force) to effect progressive effacement and dilation of the cervix prior to term gestation. Occurring at 20-37 weeks' gestation, preterm labor precedes almost half of preterm births in the United States. More particularly, preterm birth is a major public health problem with approximately 1 in 9 babies born prematurely, leading to increased rates of infant morbidity and mortality. Preterm labors remain unexplained and the rate of preterm delivery remains unchanged at about 5%. Despite the widespread use of tocolytic drugs, there has not been any documented decrease in the rate of preterm birth in recent years. This is largely due to the fact that there is still a very limited understanding of the physiology of parturition and causes of preterm labor. Although the etiology of preterm birth is multifactorial, the mechanisms underlying inflammation associated uterine contractility are a common theme.

Progesterone, a major steroid hormone that is naturally produced by the body and which levels increase during pregnancy, and its analogues are the primary therapeutic options for the prevention of preterm birth. Investigations of 17-hydroxyprogesterone caproate (17-OHPC) have demonstrated efficacy in the prevention of recurrent preterm birth in singleton pregnancies. Further, micronized progesterone has been proposed to decrease the rates of preterm birth and neonatal morbidity in pregnant women with shortened cervical length. The mechanisms underlying the decreased rate of preterm birth are not well elucidated. Further, while it is known that progesterone is primarily metabolized by cytochrome P450 3A (CYP3A) into two metabolites, 6β-hydroxyprogesterone (6β-OHP) and 16α-hydroxyprogesterone (16α-OHP), the physiologic role of progesterone metabolism and actions of endogenous metabolites have not been well studied.

Based on the foregoing, there is a need in the art to better understand preterm labor and means for predicting and modulating preterm labor. It would be further advantageous if methods could be used on a genomic level to modulate inflammation in other tissues of a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIG. 2A: Uterine horns were isolated and suspended in a tissue organ bath at 0.5 g of tension. Once equilibrated, selected progestin treatments were added in successively increasing concentrations from $10^{-9}$ to $10^{-6}$ mol/L in 20-minute intervals to assess effect on spontaneous contractile activity (progesterone treatment, bottom panel). The contralateral horn from each mouse was treated with a matching ethanol vehicle (top panel). All contraction responses were measured and reported as the area under the contraction curve (AUC), normalized to the AUC of the spontaneous contraction pattern that preceded treatment. FIG. 2B: Treatment effect on oxytocin-induced contractility was assessed by exposing horns to selected progestin treatments ($10^{-6}$ mol/L), followed by increasing doses of oxytocin (Oxt) (1, 10, 50, and 100 nmol/L) in 10-minute intervals (bottom panel). The contralateral horn from each mouse was treated with a matching ethanol vehicle (top panel). Contraction responses were measured and reported as described above.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The cytochrome P450 3A (CYP3A) family of enzymes is a major source of xenobiotic metabolism in both the mother and the fetus. The ontogeny of CYP3A involves a change in expression from CYP3A7 during the fetal period to CYP3A4 and CYP3A5 after the first year of life. Cytochrome P450 3A is the dominant enzyme for metabolic oxidation of xenobiotics in the fetus, comprising 50% of the total cytochrome P450 content in the fetal liver.

Figure 1:
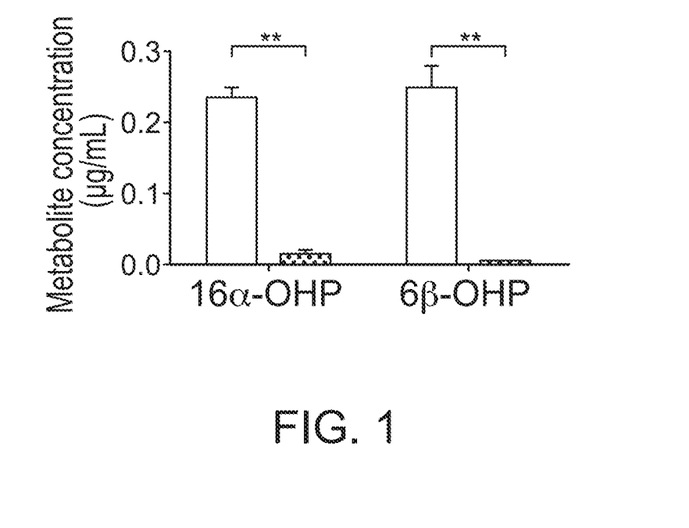
FIG. 1 depicts CYP3A production of 16α-OHP and 6β-OHP in human liver microsomes (HLMs). CYP3A production is inhibited by exposure to ketoconazole ($p<0.01$), a CYP3A inhibitor.

In vitro, microsome assays to approximate formation enzyme kinetics identified CYP3A4 and CYP3A5 as the primary isoforms responsible for production of 6β-hydroxy-progestrone (6β-OHP) and 16α-hydroxyprogestrone (16αOHP), with production of 6β-OHP favored in human liver microsomes (Table 1; FIG. 1). Notably, CYP3A4 and CYP3A5 have well-characterized polymorphisms that may affect enzyme function and metabolite formation (Table 1). One of these polymorphisms, CYP3A5*3, results in a significantly higher prevalence of non-functional protein in Caucasian vs. African-American populations (Table 2).

TABLE 1

Enzyme kinetic parameters for cytochrome P450 CYP3A catalyzed progesterone metabolism

| | 16α-OHP | | | 6β-OHP | | |
|---|---|---|---|---|---|---|
| Enzyme | Vmax | Km | CLint | Vmax | Km | CLint |
| CYP3A4 | 19.2 ± 1.1 | 15.6 ± 4.3 | 1.3 | 22.3 ± 1.1 | 9.7 ± 2.7 | 2.3 |
| CYP3A5 | 0.2 ± 0.3 | 72.5 ± 24.3 | 0.003 | 16.2 ± 1.1 | 60.2 ± 11.9 | 0.009 |
| CYP3A7 | 0.1 ± 0.03 | 43.8 ± 31.0 | 0.003 | 0.2 ± 0.03 | 44.4 ± 23.5 | 0.004 |

TABLE 2

Population frequencies of select CYP3A polymorphisms

| CYP3A isoform | Caucasian (%) | African American (%) | Other (%) | Effect |
|---|---|---|---|---|
| CYP3A4*22 | 8 | 4 | 4 (Asian) | Decreased activity |
| CYP3A5*1 | 5-10 | >60 | | Active allele |
| CYP3A5*3 | 88-97 | 12-35 | | Nonfunctional protein |
| CYP3A5*6 | 0 | 12 | 15-25 (African) | Nonfunctional protein |

Modulating Uterine Contractility

In accordance with one aspect of the present disclosure, methods have been discovered that allow for the modulation of uterine contractility. As used herein, "modulate", "modulation", and "modulating" refer to the ability of the methods to adjust or maintain contractility of a subject's uterus at a desired level in terms of at least one of contractile force/intensity and contractile frequency. For example, in one embodiment, the subject is a pregnant woman which is in preterm labor. In this embodiment, it is desirable to decrease uterine contractility to prevent or delay preterm delivery. In another embodiment, the subject is a pregnant woman and the desire is to increase contractible force and/or frequency to induce labor.

Generally, the methods for modulating uterine contractibility include administering a progesterone metabolite to a subject in need thereof. As used herein, "subject in need thereof" refers to a subset of subjects in need of increasing or decreasing uterine contractile force and/or uterine contractile frequency. In one embodiment, subjects that are in specific need may include pregnant subjects who are susceptible to, or at elevated risk of, experiencing preterm labor and preterm delivery. Subjects may be susceptible to, or at elevated risk of, experiencing symptoms of preterm labor and preterm delivery due to past experiences of preterm labor and/or preterm delivery, family history, age, environment, and/or lifestyle. More particularly, a pregnant subject at elevated risk of preterm labor and/or preterm delivery includes pregnant subjects having one or more of the following: infection/inflammation of the uterus, decidual hemorrhage, maternal stress, cervical insufficiency, uterine distension, placental dysfunction, and preterm premature rupture of membranes (PPROM).

In another embodiment, subjects that are in specific need may include pregnant subjects in need of inducing labor. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

Suitable progesterone metabolites for administration to the subject include 17-hydroxyprogesterone caproate (17-OHPC), 2α-hydroxyprogesterone (2α-OHP), 6β-hydroxyprogesterone (6β-OHP), 16α-hydroxyprogesterone (16αOHP), and combinations thereof.

In one particular embodiment, it is desired to increase contractile force and/or contractile frequency in the subject, such as a subject in need of inducing labor. In this embodiment, the methods of the present disclosure include administering 6β-OHP as the progesterone metabolite.

In another embodiment, it is desired to decrease contractile force and/or contractile frequency in the subject, such as a subject at risk of preterm labor and/or preterm delivery. In this embodiment, the methods of the present disclosure include administering a progesterone metabolite selected from the group consisting of 17-OHPC, 16αOHP, and combinations thereof.

Mitigating Inflammation

In accordance with another aspect of the present disclosure, methods have been discovered that allow for the mitigation of inflammation in various tissue types of a subject. Advantageously, the methods of the present disclosure involve the use of progesterone metabolites to surprisingly allow for mitigation of both systemic and localized inflammation in subjects. Inflammation may be due to infection within the tissues or any other cause of inflammation known in the art.

In one embodiment, the methods provide for mitigation of localized inflammation such as in tissue macrophages. In one particular embodiment, the methods include administration of a progesterone metabolite to a subject suffering from inflammation and/or infection of uterine smooth muscle cells (UtSMC) to reduce the inflammatory response in the cells.

In another embodiment, the methods include administering a progesterone metabolite to a subject suffering from systemic inflammation. For example, the methods may be used to treat a subject suffering inflammatory response in monocytes.

Suitable progesterone metabolites for administration to the subject include 6β-hydroxyprogesterone (6β-OHP), 16α-hydroxyprogesterone (16αOHP), and combinations thereof.

The term "administering" as used herein includes all means of introducing the progesterone metabolite(s) described herein to the subject, including, but not limited to, oral (po), intravenous (iv), intramuscular (im), subcutaneous (sc), parenteral, transdermal, inhalation, buccal, ocular, sublingual, vaginal, rectal, and the like. The metabolite(s) described herein may be administered in unit dosage forms and/or formulations containing conventional nontoxic pharmaceutically-acceptable carriers, adjuvants, and vehicles.

Illustrative formats for oral administration include tablets, capsules, elixirs, syrups, and the like.

Illustrative routes for parenteral administration include intravenous, intraarterial, intraperitoneal, epidural, intraurethral, intrasternal, intramuscular and subcutaneous, as well as any other art recognized route of parenteral administration.

Illustratively, administering includes local use, such as when administered locally to the site of inflammation, infection, injury, or defect, or to a particular organ (e.g., uterus) or tissue system. Illustrative local administration may be performed during open surgery, or other procedures when the site of inflammation, infection, injury, or defect is accessible. Alternatively, local administration may be performed using parenteral delivery where the metabolite(s) described herein is deposited locally to the site without general distribution to multiple other non-target sites in the subject being treated. It is further appreciated that local administration may be directly in the injury site, or locally in the surrounding tissue. Similar variations regarding local delivery to particular tissue types, such as organs, and the like, are also described herein.

In some embodiments, a therapeutically effective amount of progesterone metabolite in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the metabolite can be administered in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The progesterone metabolite-containing formulations may contain anywhere from about 0.1% by weight to about 99.9% by weight active ingredients, depending upon the selected dose and dosage form.

Diagnostic Methods

In yet another embodiment, the present disclosure is directed to use of the progesterone metabolites as biomarkers to detect the risk of a pregnant woman to enter into preterm labor.

The term "biomarker" as used herein refers to a molecule to be used as a target for analyzing a subject's test sample. In one embodiment, examples of such molecular targets are proteins or polypeptides. Proteins or polypeptides used as a marker in the present disclosure are contemplated to include naturally occurring variants of said protein as well as fragments of said protein or said variant, in particular, immunologically detectable fragments. Immunologically detectable fragments may comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present disclosure. In addition, or in the alternative, a marker polypeptide or a variant thereof may carry a post-translational modification. Exemplary posttranslational modifications are glycosylation, acylation, and phosphorylation.

The term "label" as used herein refers to any substance that is capable of producing a signal via direct or indirect detection. For direct detection, the labeling group or label suitable for use in the present disclosure can be selected from any known detectable marker groups, but are not limited to, chromogens, fluorescent, chemiluminescent groups (e.g. acridinium esters or dioxetanes), electrochemiluminescent compounds, catalysts, enzymes, enzymatic substrates, dyes, fluorescent dyes (e.g. fluorescein, coumarin, rhodamine, oxazine, resorufin, cyanine and derivatives thereof), colloidal metallic and nonmetallic particles, and organic polymer latex particles. Other examples of labeling groups are luminescent metal complexes, such as ruthenium or europium complexes, enzymes, e.g. as used for ELISA, and radioisotopes.

The term "sample" or "test sample" as used herein refers to a biological sample obtained from a subject for the purpose of evaluation in vitro. In the methods of the present disclosure, the sample may include any body fluid. Exemplary samples are body fluids, such as serum, plasma, or whole blood.

A reference ratio is established in a control sample. The control sample may be an internal or an external control sample. In one embodiment, an internal control sample is used, i.e. the marker level(s) is(are) assessed in the test sample as well as in one or more other sample(s) taken from the same subject to determine if there are any changes in the level(s) of said marker(s). In another embodiment, an external control sample is used. For an external control sample, the presence or amount of a marker in a sample derived from the subject is compared to its presence or amount in a subject known to suffer from, or known to be at risk of, a given condition; or an individual known to be free of a given condition, i.e., "normal individual". For example, a marker level in a subject sample can be compared to a level known to be associated with preterm labor.

In one particular embodiment, the present disclosure relates to an in vitro method of diagnosing a subject as being at elevated risk for preterm labor, the method including: measuring a concentration of 6β-hydroxyprogesterone (6β-OHP) and a concentration of 16α-hydroxyprogesterone (16αOHP) in a sample obtained from the subject to determine a ratio of 6β-hydroxyprogesterone (6β-OHP)/16α-hydroxyprogesterone (16αOHP) in the subject; comparing the ratio of 6β-hydroxyprogesterone (6β-OHP)/16α-hydroxyprogesterone (16αOHP) of the subject with a reference ratio of 6β-hydroxyprogesterone (6β-OHP)/16α-hydroxyprogesterone (16αOHP); and providing a diagnosis of the subject being at an elevated risk for preterm labor if the ratio of 6β-hydroxyprogesterone (6β-OHP)/16α-hydroxyprogesterone (16αOHP) in the sample determined in said step of measuring is greater than the reference ratio.

According to some embodiments, the marker progesterone metabolite (e.g., 6β-hydroxyprogesterone (6β-OHP) or 16α-hydroxyprogesterone (16αOHP)) is specifically measured in vitro from a liquid sample by use of a specific binding agent. In some embodiments according to the present disclosure, the concentration of 6β-hydroxyprogesterone (6β-OHP) and/or 16α-hydroxyprogesterone (16αOHP) is measured. In an embodiment, the concentration of marker 6β-hydroxyprogesterone (6β-OHP) and/or 16α-hydroxyprogesterone (16αOHP) is specifically measured in vitro from a sample by use of a specific binding agent.

In yet another embodiment, the present disclosure is directed to use of the progesterone metabolites as biomarkers for susceptibility for systemic infection.

In one particular embodiment, the present disclosure relates to an in vitro method of diagnosing a subject as being susceptible for systemic infection, the method including: measuring a concentration of 6β-hydroxyprogesterone (6β-OHP) and a concentration of 16α-hydroxyprogesterone (16αOHP) in a sample obtained from the subject to determine a ratio of 6β-hydroxyprogesterone (6β-OHP)/16α-hydroxyprogesterone (16αOHP) in the subject; comparing the ratio of 6β-hydroxyprogesterone (6β-OHP)/16α-hydroxyprogesterone (16αOHP) of the subject with a reference ratio of 6β-hydroxyprogesterone (6β-OHP)/16α-hydroxyprogesterone (16αOHP); and providing a diagnosis of the subject being susceptible for systemic infection if the ratio of 6β-hydroxyprogesterone (6β-OHP)/16α-hydroxyprogesterone (16αOHP) in the sample determined in said step of measuring is greater than the reference ratio.

According to some embodiments, the marker progesterone metabolite (e.g., 6β-hydroxyprogesterone (6β-OHP) or 16α-hydroxyprogesterone (16αOHP)) is specifically measured in vitro from a liquid sample by use of a specific binding agent. In some embodiments according to the present disclosure, the concentration of 6β-hydroxyprogesterone (6β-OHP) and/or 16α-hydroxyprogesterone (16αOHP) is measured. In an embodiment, the concentration of marker 6β-hydroxyprogesterone (6β-OHP) and/or 16α-hydroxyprogesterone (16αOHP) is specifically measured in vitro from a sample by use of a specific binding agent.

In yet another embodiment, the present disclosure is directed to use of the progesterone metabolites as biomarkers for susceptibility for systemic inflammation.

In one particular embodiment, the present disclosure relates to an in vitro method of diagnosing a subject as being susceptible for systemic inflammation, the method including: measuring a concentration of 6β-hydroxyprogesterone (6β-OHP) and a concentration of 16α-hydroxyprogesterone (16αOHP) in a sample obtained from the subject to determine a ratio of 6β-hydroxyprogesterone (6β-OHP)/16α-hydroxyprogesterone (16αOHP) in the subject; comparing the ratio of 6β-hydroxyprogesterone (6β-OHP)/16α-hydroxyprogesterone (16αOHP) of the subject with a reference ratio of 6β-hydroxyprogesterone (6β-OHP)/16α-hydroxyprogesterone (16αOHP); and providing a diagnosis of the subject being susceptible for systemic inflammation if the ratio of 6β-hydroxyprogesterone (6β-OHP)/16α-hydroxyprogesterone (16αOHP) in the sample determined in said step of measuring is greater than the reference ratio.

According to some embodiments, the marker progesterone metabolite (e.g., 6β-hydroxyprogesterone (6β-OHP) or 16α-hydroxyprogesterone (16αOHP)) is specifically measured in vitro from a liquid sample by use of a specific binding agent. In some embodiments according to the present disclosure, the concentration of 6β-hydroxyprogesterone (6β-OHP) and/or 16α-hydroxyprogesterone (16αOHP) is measured. In an embodiment, the concentration of marker 6β-hydroxyprogesterone (6β-OHP) and/or 16α-hydroxyprogesterone (16αOHP) is specifically measured in vitro from a sample by use of a specific binding agent.

A specific binding agent is, e.g., a receptor for the metabolite, a lectin binding to the metabolite, an antibody to the metabolite, peptide bodies to the metabolite, bispecific dual binders, multispecific binders, bispecific antibody formats or multispecific antibody formats.

As the skilled artisan will appreciate the term "specific" is used to indicate that other biomolecules present in the sample do not significantly bind to the binding agent specific for the progesterone metabolite being measured. In some embodiments, the level of binding to a biomolecule other than the target molecule results in a binding affinity which is at most only 10% or less, only 5% or less only 2% or less or only 1% or less of the affinity to the target molecule, respectively. Specific binding agent may fulfill both the above minimum criteria for affinity as well as for specificity.

Examples of specific binding agents are peptides, peptide mimetics, aptamers, spiegelmers, darpins, ankyrin repeat proteins, Kunitz type domains, antibodies, single domain antibodies, and monovalent fragments of antibodies. In certain embodiments the specific binding agent is a polypeptide. In certain embodiments the specific binding agent is an antibody or a monovalent antibody fragment, for example a monovalent fragment derived from a monoclonal antibody. Monovalent antibody fragments include, but are not limited to Fab, Fab'-SH, single domain antibody, Fv, and scFv fragments.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. In certain embodiments, the specific binding agent is an antibody or a monovalent antibody fragment, for example a monovalent fragment derived from a monoclonal antibody.

The following examples further illustrate specific embodiments of the present disclosure; however, the following illustrative examples should not be interpreted in any way to limit the disclosure.

EXAMPLES

Example 1

In this Example, the progesterone metabolites 6β-OHP and 16αOHP were analyzed for their effect in modulating uterine contractility in a mouse model.

Materials and Methods Selection of Progestins

Cytochrome P450 3A has nicotinamide adenine dinucleotide phosphate-oxidase (NADPH)-dependent high catalytic activity at the 2-, 4-, 6β-, 16α-, and 16β-positions on the steroid ring structure. Monohydroxylated derivatives of progesterone at these sites were considered potential products of CYP3A metabolism. Recombinant CYP3A4 metabolism of progesterone has previously been demonstrated to produce 6β-hydroxyprogesterone (6β-OHP) and 16α-hydroxyprogesterone (16αOHP). Three candidate metabolites were used in the experimental protocol: 4-pregnen-2α-ol-3,20-dione (2α-OHP), 4-pregnen-6β-ol-3,20-dione (6β-OHP), and 4-pregnen-16α-ol-3,20-dione (16αOHP). Progesterone and 17-OHPC (4-pregnen-17-ol-3,20-dione caproate) were also selected for testing. All progestins were obtained from a chemical supply vendor (Steraloids, Newport, R.I.).

All progestins were solubilized in ethanol and then diluted in phosphate-buffered saline to the desired molar concentration. Progesterone, 17-OHPC, and 6β-OHP had an ethanol concentration of 0.001% at the $10^{-6}$ mol/L dose (0.0001% at $10^{-7}$ mol/L, 0.00001% at $10^{-8}$ mol/L, and 0.000001% at $10^{-9}$ mol/L), while 2α-OHP and 16αOHP had an ethanol concentration of 0.004% at the $10^{-6}$ mol/L dose (0.0004% at $10^{-7}$ mol/L, 0.00004% at $10^{-8}$ mol/L, and 0.000004% at $10^{-9}$ mol/L). The concentration of ethanol decreased parallel to the progestin dose in order to minimize the effect of the solvent on uterine contractility.

Experimental Model

Virgin nonpregnant wild-type C57BL/6J female mice (Jackson Labs, Bar Harbor, Me.) were obtained at 10 to 12 weeks of age and fed a standard diet. Mice were euthanized by an IACUC-approved protocol, and each of the 2 uterine horns were removed. A 1 cm×0.5 cm segment of the uterine horn was suspended using 4-0 silk suture between a stainless steel wire hook connected to a Radnoti force displacement transducer (Radnoti LLC, Monrovia, Calif.) and a glass hook inside an organ bath that served as an anchor. The bath was filled with modified Krebs buffer (118 mmol/L NaCl, 4.8 M KCl, 1.2 mmol/L $MgSO_4$, 1.2 mmol/L $KH_2PO_4$, 2.5 mmol/L $CaCl_2$, 25 mmol/L $NaHCO_3$, and 11 mmol/L glucose, pH 7.4), maintained at 37° C., and constantly bubbled with a premixed gas consisting of 20% $O_2$, 5% $CO_2$, and balance $N_2$. Uterine horns were equilibrated at 0.5 g of tension for approximately 30 minutes until a spontaneous contraction pattern was established.

A total of 60 mice were utilized to assess the effect of the selected treatments on uterine contractility, 30 in the spontaneous contraction group and 30 in the oxytocin-induced group. Six mice were in each progestin treatment group during both spontaneous and oxytocin-induced contractility arms of the study. To determine the nongenomic (acute) effect of the progestin treatments on spontaneous uterine contractility, a segment of uterine horn from each mouse was exposed to a single progestin (progesterone, 17-OHPC, 2α-OHP, 6β-OHP, or 16αOHP), while a segment of the contralateral horn was exposed to a matching dose of ethanol vehicle. After a spontaneous contraction pattern was achieved, the progestin treatment was added to the tissue organ bath in successively increasing concentrations from $10^{-9}$ to $10^{-6}$ mol/L in 20-minute intervals. At the end of the treatments, the tissue was washed in modified Krebs buffer and then exposed to KCl (60 mmol/L) to elicit a tetanic response and confirm tissue viability.

To determine the nongenomic effect of progestin treatments on oxytocin-induced uterine contractility, the uterine horns were pretreated with a single progestin at $10^{-6}$ mol/L for 10 minutes after a spontaneous contractile pattern was established. The contralateral horn from the same mouse was treated with ethanol vehicle at a matching concentration. The uterine horns were subsequently exposed to increasing concentrations of oxytocin (1, 10, 50, and 100 nmol/L) in 10-minute intervals. At the end of the oxytocin treatments, the tissue was washed and then exposed to KCl (60 mmol/L) to elicit a tetanic response and confirm tissue viability.

Statistical Analysis

Uterine contraction responses were recorded using LabChart Pro (ADInstruments, Colorado Springs, Colo.) software as the force generated with time (g×min). Baseline uterine contractility was calculated as the area under the curve (AUC) for a 10-minute period of spontaneous contractions. The AUC of the uterine contractile response to each treatment (progestin or oxytocin) was determined and expressed as a percentage of the baseline AUC observed during spontaneous contraction. Spontaneous contractions in murine uterine muscle strips have previously been shown to have a linear correlation ($r^2$=0.90) with the AUC following treatment with 1 nmol/L oxytocin. To account for repeated measurements for individual muscle strips at increasing treatment doses, a repeated measures 2-way analysis of variance model was used to compare the dose-response curves. Each dose-response curve was fit by non-linear regression and compared using an extra sum of squares F test. The mean max-fit response was compared between each progestin and vehicle control to determine maximum treatment efficacy. Half maximal inhibitory concentration (IC50; spontaneous contractility) and half maximal effective concentration (EC50; oxytocin-induced contractility) values were compared between each progestin and vehicle control to determine treatment potency. All analyses were performed using GraphPad Prism Version 6.0b for Macintosh (GraphPad Software, La Jolla, Calif.). A P value <0.05 was considered significant.

Confirmation of Progesterone Metabolites

Production of putative progestin metabolites by CYP3A was confirmed by in vitro metabolism studies. Baculovirus-inset cell-expressed human P450s (CYP3A4, CYP3A5, and CYP3A7) were purchased from Corning Inc. (Woburn, Mass.). All chemicals were of high performance liquid chromatography (HPLC) grade. Progesterone (100 µmol/L) was reconstituted with sodium phosphate buffer (100 mmol/L, pH 7.4), $MgSO_4$ (5 mmol/L), and recombinant human P450s (25 pmol). The reactions were initiated by adding NADPH (10 mmol/L), incubated for 30 minutes, and terminated with an identical volume of ice-cold acetonitrile (ACN). The reaction mixtures were centrifuged (3000 rpm×5 mm), and the supernatants were separated. An internal standard (6β-hydroxytestosterone [6β-OHT]) and citric acid (0.1 mol/L, pH 3.2) were added to each sample tube. Progesterone metabolites were extracted by mixing with 3 mL of methyl tert-butyl ether and centrifugation (3000 rpm×5 min). The organic phase was removed and evaporated prior to reconstitution in 100 µL of mobile phase A, from which 70 µL was injected onto the HPLC/uV/visible system as described subsequently.

Serial dilutions of 16αOHP and 6β-OHP were prepared (1 mg/mL, methanol) for a standard curve. The total volume of the standards was the same as the incubation reaction volume in sodium phosphate buffer (100 mmol/L, pH 7.4). Extraction and separation of progestin standards were performed as described earlier. The 0 µg/mL standard contained only the internal standard, and the highest concentrations were based on the estimated metabolite formation. The quality controls were performed in triplicate along with standards.

A profile of metabolites produced by progesterone was determined by HPLC/uV detection (254 nm). An agilent column Luna 5u C18 (2) 100A (250×4.6 mm) was used throughout the experiments. Samples and standards were run on a gradient (mobile phase B: 0 min 40%; 1 mm 40%; 28 min 95%; 28.1 min 40%, and 30 mm 40%) with mobile phase A 0.25%/10%/90% (acetic acid/$ACN/H_2O$) and mobile phase B 0.25%/90%/10% (acetic acid/$ACN/H_2O$) at a flow rate 1.0 mL/min. Chromatographic peaks and retention times were confirmed by comparison with the standard curve. The AUCs with corresponding retention times (6β-OHT: 5.74 minutes, 16αOHP: 8.74 minutes, and 6β-OHP: 11.44 minutes) were collected.

Results

Figure 2A:
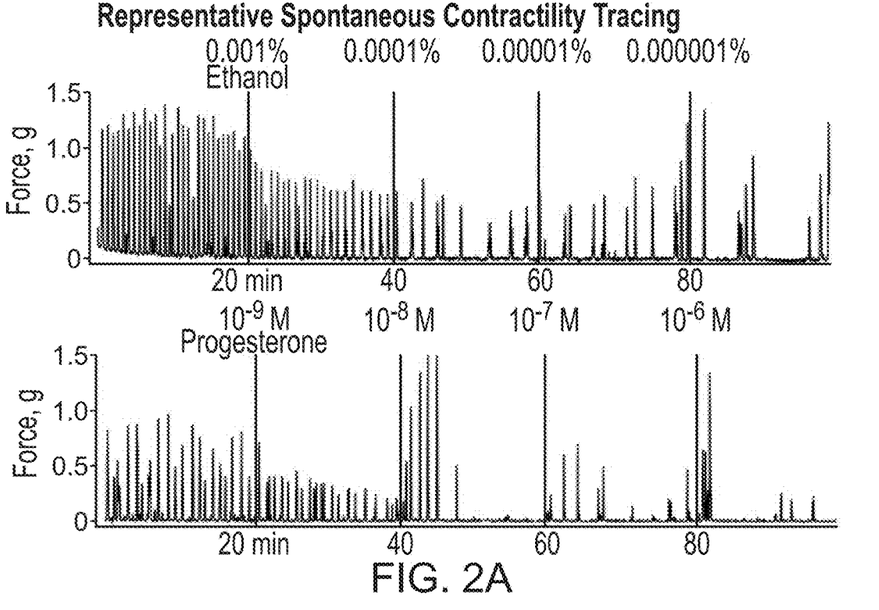
FIGS. 2A & 2B are representative contraction tracings of uterine horns from wild-type (WT) C57BL/6J female mice.

A representative tracing of an isolated uterine horn response to progesterone and vehicle control from the spontaneous uterine contractility experiment is shown in FIG. 2A. Horns treated with progesterone demonstrated a reduced spontaneous contractile force compared to vehicle control (43.9% vs 64.1% of baseline AUC, P=0.02) at maximal treatment dose. No significant difference in spontaneous contractile force was seen at maximal treatment dose in horns treated with 17-PHPC (P=0.16), 2α-OHP (P=0.78), 6β-OHP (P=0.53), or 16αOHP (P=0.27) compared with the vehicle control. A summary of spontaneous contractile force findings is provided in Table 3.

TABLE 3

Summary of spontaneous contractility data (schema for contractility experiment is shown in FIG. 2A).

| Treatment | Contractile Force (% of baseline) | | P-Value | Contractile Frequency/ 10 min (% of baseline) | | P-Value |
|---|---|---|---|---|---|---|
| | Drug | Vehicle | | Drug | Vehicle | |
| Progesterone | 43.9% | 64.1% | 0.02 | 48% | 47.9% | 0.99 |
| 17-hydroxy-progesterone caproate (17-OHPC) | 50.4% | 39.7% | 0.16 | 57.9% | 54.5% | 0.68 |
| 2α-hydroxy-progesterone (2α-OHP) | 37.9% | 39.3% | 0.78 | 53.7% | 55.9% | 0.77 |
| 6β-hydroxy-progesterone (6β-OHP) | 45% | 49.8% | 0.53 | 46.2% | 55.9% | 0.27 |
| 16α-hydroxy-progesterone (16α-OHP) | 37.2% | 28.5% | 0.27 | 57% | 53.3% | 0.70 |

As shown in Table 3, 6β-OHP was observed to increase oxytocin-induced uterine contractility, while 16αOHP decreased oxytocin-induced uterine contractility.

Figure 2B:
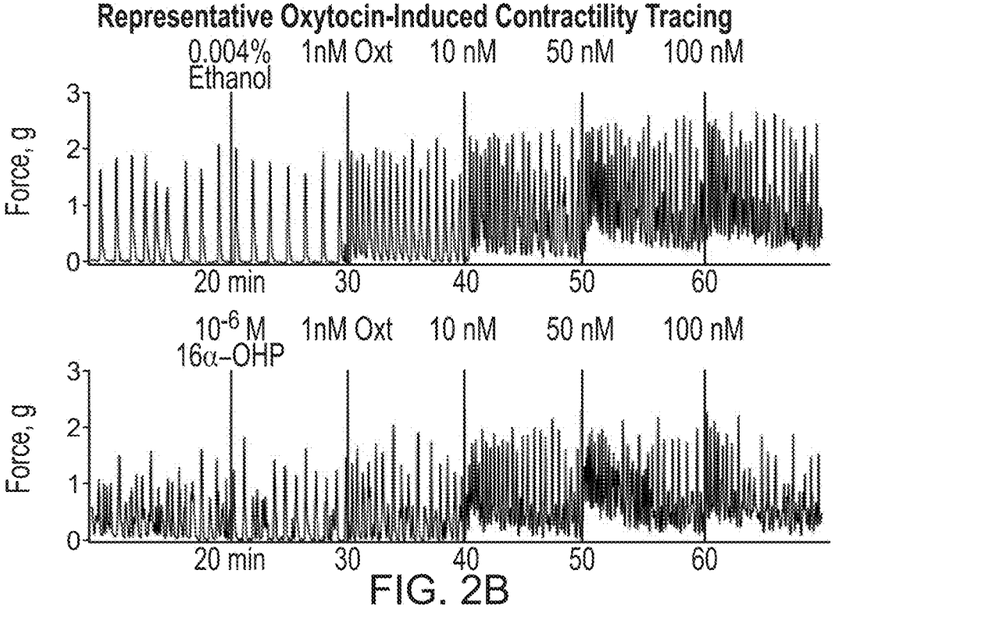
Figure 3A:
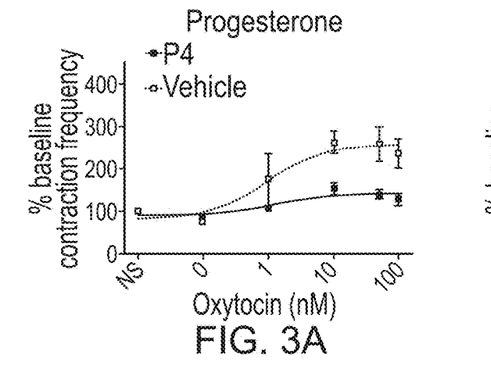
FIGS. 3A-3E are dose-response curves of oxytocin-induced uterine contractile frequency following progestin pretreatment. Contraction frequency decreased significantly at maximal oxytocin dose (100 nmol/L) after pretreatment of uterine horns with progesterone (FIG. 3A, P=0.02), 17-OHPC (FIG. 3B, P=0.03), 6β-hydroxyprogesterone (FIG. 3D, P 1/4 0.05), or 16α-hydroxyprogesterone (FIG. 3E, P=0.03) but not 2α-hydroxyprogesterone (FIG. 3C, P=0.12) compared to control. Error bars depict standard error (SE).
Figure 3B:
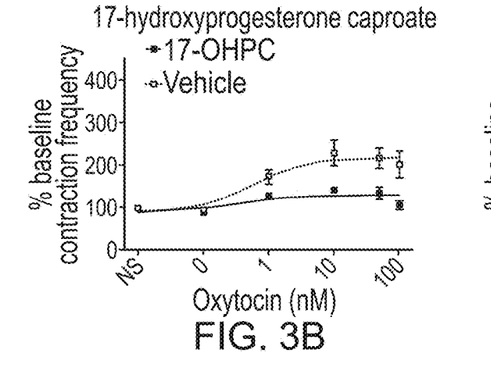
Figure 3C:
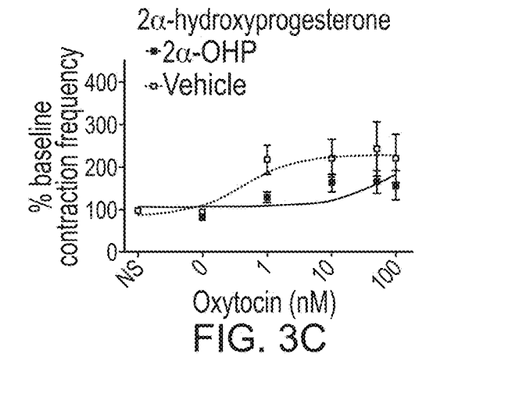
Figure 3D:
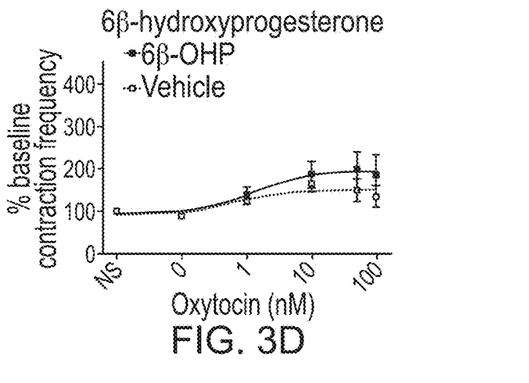
Figure 3E:
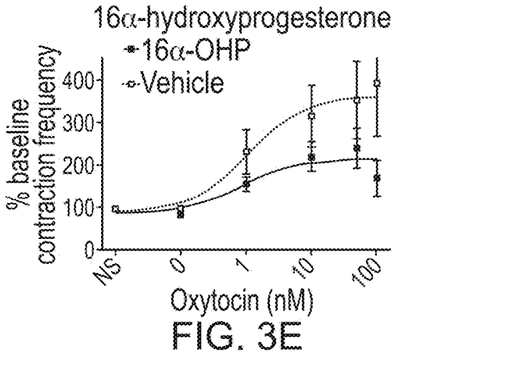

A representative tracing of an isolated uterine horn response to 16α-OHP and vehicle control from the oxytocin-induced uterine contractility experiment is shown in FIG. 2B. Horns pretreated with progesterone demonstrated a significant decrease in contractile force as measured by AUC at maximal oxytocin dose compared to vehicle control (266.8% vs 497.5%, P=0.02). Uterine strips treated with 17-OHPC also demonstrated a significant decrease in contractile force compared to vehicle control (218.4% vs 415.7%, P=0.04). There were no differences in oxytocin-induced contractile force at maximal dose (100 nmol/L) in horns pretreated with 2α-OHP (P=0.34), 6β-OHP (P=0.91), or 16αOHP (P=0.07) compared to vehicle control. A summary of oxytocin-induced contractile force findings is provided in Table 4.

TABLE 4

Summary of oxytocin-induced contractility data (schema for contractility experiment is shown in FIG. 2B)

| Treatment | Contractile Force (% of baseline) | | P-Value | Contractile Frequency/ 10 min (% of baseline) | | P-Value |
|---|---|---|---|---|---|---|
| | Drug | Vehicle | | Drug | Vehicle | |
| Progesterone | 266.8% | 497.5% | 0.02 | 141% | 258.2% | 0.02 |
| 17-hydroxy-progesterone caproate (17-OHPC) | 218.4% | 415.7% | 0.04 | 130.2% | 219.4% | 0.03 |
| 2α-hydroxy-progesterone (2α-OHP) | 329.5% | 390.7% | 0.34 | 168.9% | 237.6% | 0.12 |
| 6β-hydroxy-progesterone (6β-OHP) | 267.6% | 262.6% | 0.91 | 196.1% | 151.6% | 0.05 |
| 16α-hydroxy-progesterone (16α-OHP) | 301.6% | 442% | 0.07 | 216.9% | 364.7% | 0.03 |

Spontaneous uterine contraction frequency was not significantly decreased after treatment with progesterone (P=0.99), 17-OHPC (P=0.68), 2α-OHP (P=0.77), 6β-OHP (P=0.27), or 16αOHP (P=0.70) at maximal treatment dose compared to vehicle control. However, oxytocin-induced contraction frequency decreased significantly after pretreatment with progesterone (141% vs 258% of baseline contraction frequency, P=0.02), 17-OHPC (130% vs 219%, P=0.03), or 16αOHP (217% vs 365%, P=0.03) but not 2α-OHP (P=0.12) compared to control (FIGS. 3A-3E). 6β-hydroxyprogesterone demonstrated an increase in oxytocin-induced contraction frequency (196% vs 152%, P=0.05) compared to control.

The potency of each progestin treatment and matched vehicle control was compared through $IC_{50}$ and $EC_{50}$ values, as listed in Table 5. All progestin treatments had $IC_{50}$ values <1 nmol/L in spontaneous contractile force dose-response curves and <1 to 10 nmol/L in spontaneous contractile frequency curves. A greater range existed for $EC_{50}$ values of progestin treatments in oxytocin-induced experiments. The $EC_{50}$ values for oxytocin-induced contractile strength curves ranged from 5 nmol/L to 150 nmol/L and from 3 nmol/L to 650 nmol/L for frequency curves. None of the $IC_{50}$ or $EC_{50}$ values of progestin treatments significantly differed from matched vehicle controls in dose-response curves.

TABLE 5

Comparison of Potency of Progestin Treatments and Matched Vehicle Controls by $IC_{50}$ and $EC_{50}$ Values in Dose-Response Curves

| Treatment | Contractile Force | | | Contractile Frequency | | |
|---|---|---|---|---|---|---|
| Spontaneous | IC50, nmol/L | 95% CI | P Value | IC50, nmol/L | 95% CI | P Value |
| Progesterone | 0.31 | 0.05-1.90 | .54 | 6.58 | 0.78-55.82 | .52 |
| Vehicle | 0.90 | 0.04-18.26 | | 1.46 | 0.21-9.89 | |
| 17-OHPC | 0.78 | 0.15-3.92 | .96 | 0.31 | 0.01-8.77 | .68 |
| Vehicle | 0.28 | 0.03-2.29 | | 0.55 | 0.04-7.86 | |
| 2α-OHP | 0.32 | 0.10-1.04 | .35 | 0.55 | 0.05-5.84 | .8 |
| Vehicle | 0.71 | 0.27-1.86 | | 0.99 | 0.12-8.46 | |
| 6β-OHP | 0.48 | 0.08-2.97 | .59 | 4.10 | 0.65-25.80 | .68 |
| Vehicle | 0.32 | 0.04-2.79 | | 6.76 | 0.99-46.40 | |
| 16α-OHP | 0.77 | 0.23-2.60 | .84 | 0.74 | 0.06-9.57 | .94 |
| Vehicle | 0.38 | 0.07-2.19 | | 0.66 | 0.04-11.74 | |
| Oxytocin induced | EC50, nmol/L | 95% CI | P Value | EC50, nmol/L | 95% CI | P Value |
| Progesterone | 9.76 | 0.76-125.4 | .97 | 11.34 | 0.49-263.6 | .91 |
| Vehicle | 10.65 | 0.72-158.4 | | 9.42 | 1.10-81.04 | |
| 17-OHPC | 8.43 | 2.9-24.52 | .89 | 3.26 | 0.18-58.09 | .72 |
| Vehicle | 10.80 | 1.22-96.00 | | 5.73 | 1.03-32.05 | |
| 2a-OHP | 68.24 | 11.68-398.7 | .92 | 645.7 | 103.6-4024 | .74 |
| Vehicle | 32.88 | 4.99-216.8 | | 4.29 | 0.18-102.0 | |
| 6O-OHP | 20.94 | 2.16-203.0 | .93 | 12.85 | 0.75-220.1 | .73 |
| Vehicle | 27.26 | 2.77-267.9 | | 6.71 | 0.32-142.6 | |
| 16a-OHP | 142.50 | 28.13-721.7 | .99 | 8.46 | 0.83-86.46 | .89 |
| Vehicle | 11.65 | 0.49-277.2 | | 10.81 | 1.11-105.7 | |

Figure 4A:
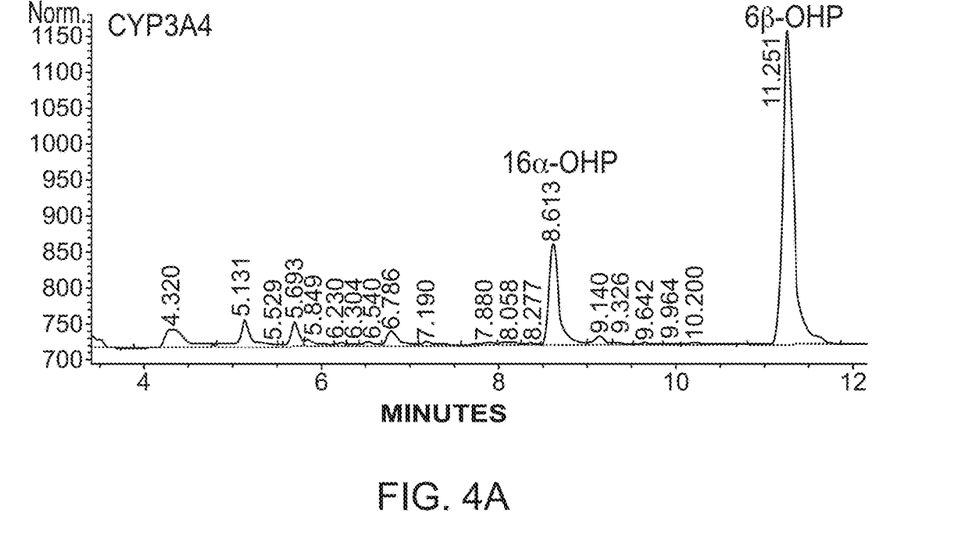
FIGS. 4A-4C depict chromatograms of metabolites formed from incubation of progesterone with CYP3A4 (FIG. 4A), CYP3A5 (FIG. 4B), and CYP3A7 (FIG. 4C). Peaks corresponding to 6β-hydroxyprogesterone and 16α-hydroxyprogesterone are labeled.
Figure 4B:
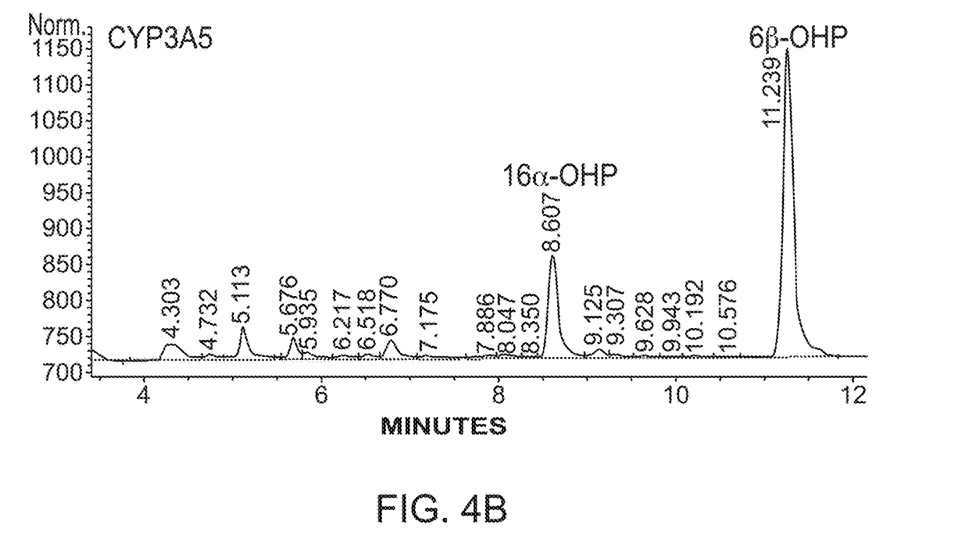
Figure 4C:
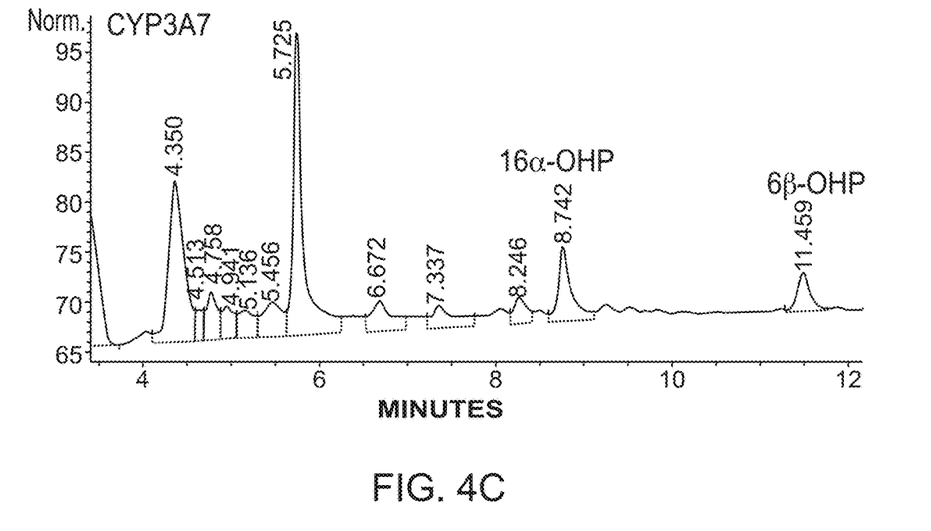

Endogenous production of the progesterone metabolites tested was confirmed in vitro. The chromatographic profile of metabolites formed from incubation of progesterone with recombinant CYP3A4, CYP3A5, and CYP3A7 is shown in FIGS. 4A-4C. A peak for 16αOHP appeared at approximately 8.6 minutes, consistent with commercial standards. Likewise, 6β-OHP appeared at approximately 11.3 minutes. Both 16αOHP and 6β-OHP were identified as products of each CYP3A isoform tested. Overlap was seen between the peaks for 2α-OHP and 17α-hydroxyprogesterone at approximately 14-minute region (not shown). Progesterone was seen to elute at 20.7 minutes (not shown).

Example 2

In this Example, the effect of progesterone metabolites 16αOHP and 6β-OHP on inflammation in primary uterine smooth muscle cells (UtSMC) was analyzed.

UtSMC were cultured in the presence of DMSO and one of the following: (1) progesterone; (2) hematopoietic progenitor cells (HPC); (3) 6β-OHP; and (4) 16αOHP. Lipopolysaccharide (LPS) was then added to the culture to stimulate an immune inflammatory reaction. Experiments were performed in triplicate.

Figure 5A:
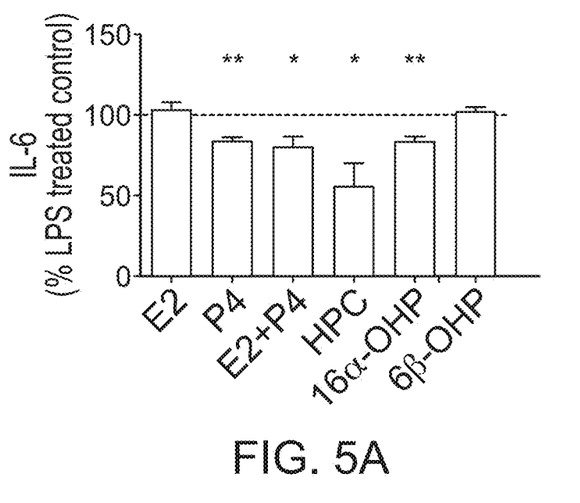
FIGS. 5A & 5B are graphs depicting the effect of progesterone metabolites 16αOHP and 6β-OHP on inflammation in primary uterine smooth muscle cells (UtSMC). UtSMC stimulated with LPS demonstrated reduced IL-6 production with 16αOHP pretreatment, but not with 6β-OHP (FIG. 5A). UtSMC stimulated with TNF-α demonstrated decreased IL-6 production after pre-treatment with both 16αOHP and 6β-OHP (FIG. 5B).

As shown in FIG. 5A, UtSMC treated with DMSO+LPS (positive control) produced IL-6 levels nearly 4-fold higher than with DMSO alone (121.7 vs. 32.4 pg/mL). Relative to the LPS positive control, IL-6 significantly declined after pre-treatment with P4 (100.3 pg/mL, 83% of positive control, p=0.003), E2/P4 (95.6 pg/mL, 80%, p=0.042), HPC (70.6 pg/mL, 55%, p=0.038), and 16αOHP (98.7 pg/mL, 83%, p=0.006), but not after pre-treatment with E2 alone (126 pg/mL, 103%, p=0.58) or 6β-OHP (125.4 pg/mL, 102%, p=0.54).

Figure 5B:
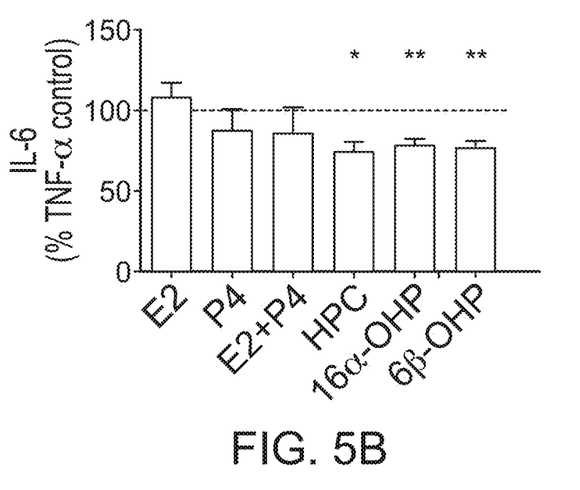

As shown in FIG. 5B, UtSMC stimulated with TNF-α demonstrated decreased IL-6 production after pre-treatment with both 16αOHP and 6β-OHP.

Example 3

In this Example, flow cytometry of a monocyte-derived macrophage population pre-treated with progesterone metabolites was conducted.

Figure 6A:
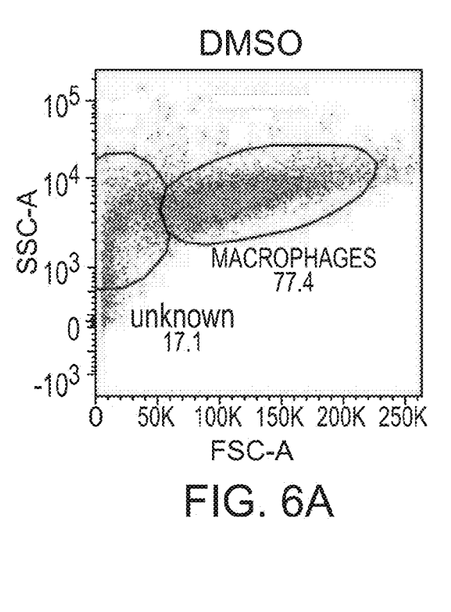
FIGS. 6A-6C depict flow cytometry of a monocyte-derived macrophage population pre-treated with progesterone metabolites. THP-1 monocyte cells were pre-treated with progesterone metabolites 16αOHP and 6β-OHP for 24 hours, then stimulated to differentiate to macrophages by exposure to PMA. A decrease in the macrophage population/phenotype was observed in the presence of progesterone metabolites 16αOHP and 6β-OHP compared to a DMSO treated control population.
Figure 6B:
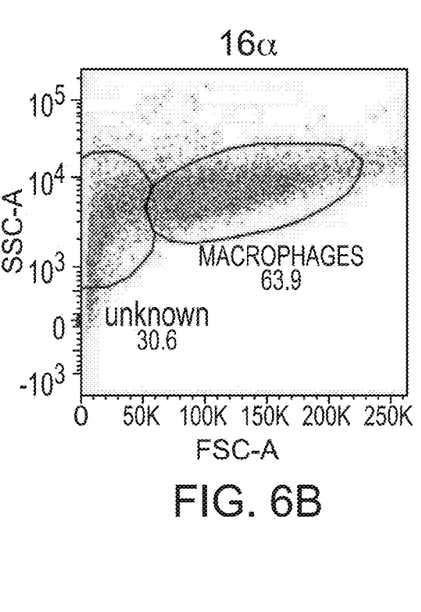
Figure 6C:
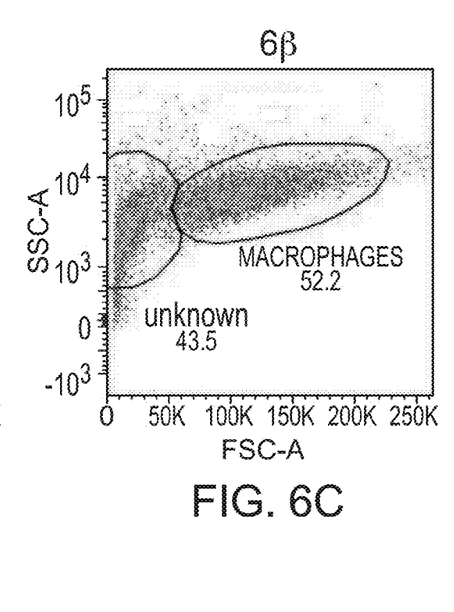

THP-1 monocyte cells were pre-treated with progesterone metabolites 16αOHP and 6β-OHP for 24 hours, then stimulated to differentiate to macrophages by exposure to phorbol 12-myristate 13-acetate (PMA). As shown in FIGS. 6A-6C, a decrease in the macrophage population/phenotype was observed in the presence of progesterone metabolites 16αOHP and 6β-OHP compared to a DMSO treated control population. Notably, macrophages comprised only 52% of the total population after treatment with 6β-OHP compared to 77% of the total population in the DMSO control.

Example 4

In this Example, monocyte-derived macrophage populations after pre-treatment with progesterone and progesterone metabolites were characterized.

Figure 7:
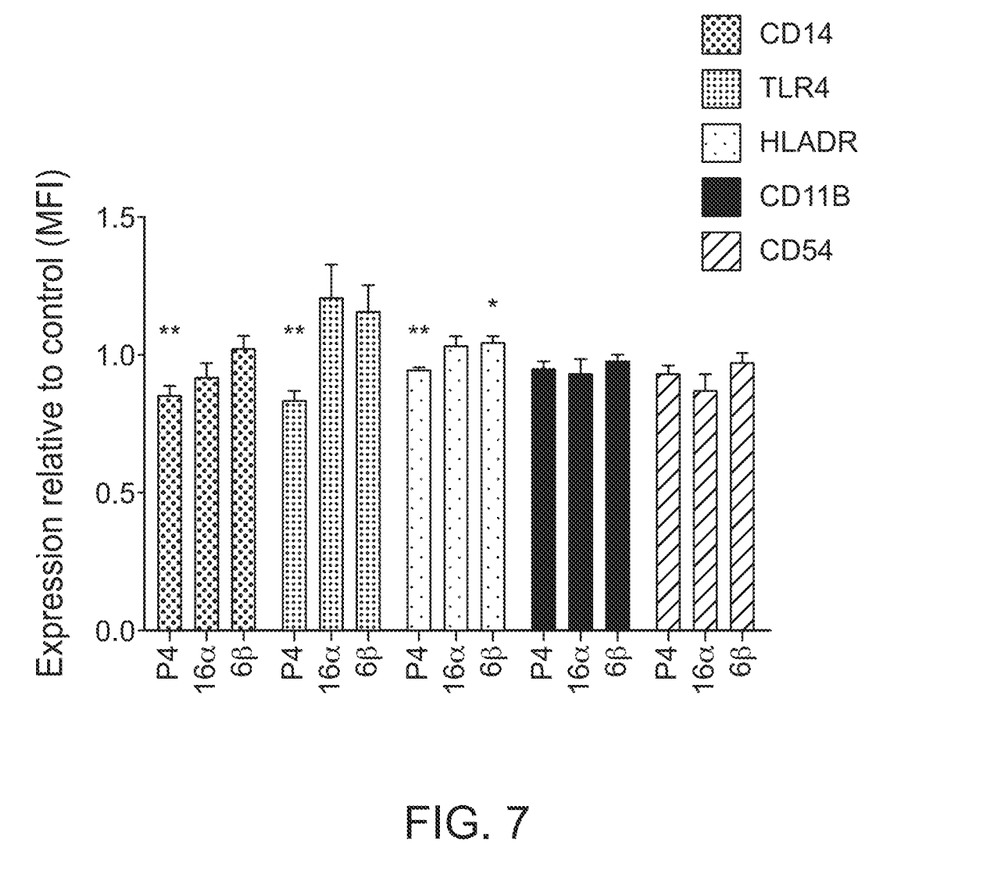
FIG. 7 is a graph depicting characterization of monocyte-derived macrophage populations after pre-treatment with progesterone and progesterone metabolites. Expression of macrophage cell surface markers is illustrated relative to DMSO treated control. Pre-treatment with progesterone decreased expression of cell surface markers involved in immune response (CD14, TLR4, and HLA-DR), but this effect was not seen in cells pre-treated with 16αOHP or 6β-OHP.

Expression of macrophage cell surface markers is illustrated relative to DMSO treated control (see FIG. 7). Pre-treatment with progesterone decreased expression of cell surface markers involved in immune response (CD14, TLR4, and HLA-DR), but this effect was not seen in cells pre-treated with 16αOHP or 6β-OHP.

Example 5

In this Example, the effect of progesterone metabolites on the LPS-induced inflammatory response in monocytes was analyzed. Particularly, NF-κB pathway activation in THP-1 monocytes stimulated with LPS after pre-treatment with progesterone and progesterone metabolites was analyzed.

Figure 8A:
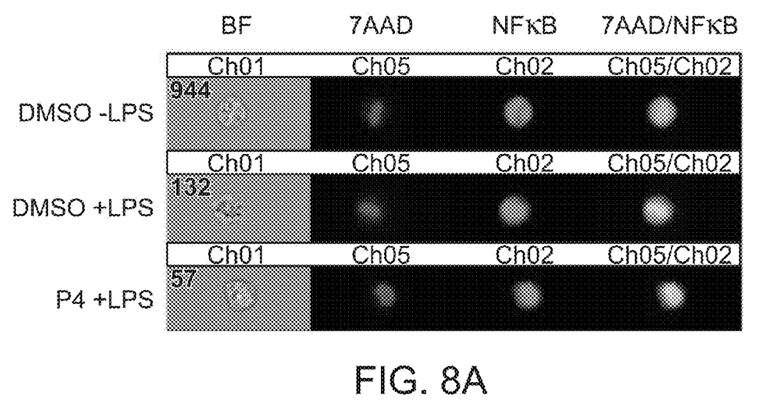
FIGS. 8A-8B depicts the summary of NF-κB pathway activation in THP-1 monocytes stimulated with LPS after pre-treatment with progesterone and progesterone metabolites. Imaging flow cytometry (FIG. 8A) illustrates representative cells with nuclear fluorescence (7AAD, red) and cytoplasmic NK-κB fluorescence (green). Monocytes not stimulated with LPS demonstrate separation of the fluorescent markers. LPS stimulation results in NF-κB migration into the nucleus, visualized as a yellow nuclear color and quantified by the median similarity score. Pre-treatment of monocytes with progesterone and progesterone metabolites did not affect the median similarity score (FIG. 8B).
Figure 8B:
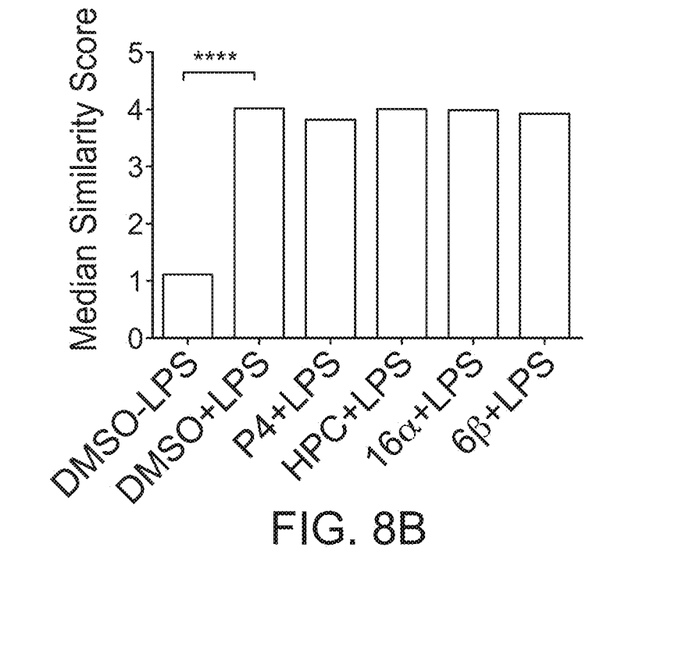

Imaging flow cytometry (FIG. 8A) illustrates representative cells with nuclear fluorescence (7AAD, red) and cytoplasmic Nκ-KB fluorescence (green). Monocytes not stimulated with LPS demonstrated separation of the fluorescent markers. LPS stimulation resulted in NF-κB migration into the nucleus, visualized as a yellow nuclear color and quantified by the median similarity score. As shown in FIG. 8B, pre-treatment of monocytes with progesterone and progesterone metabolites did not affect the median similarity score.

Example 6

In this Example, the effect of progesterone and progesterone metabolites (16αOHP and 6β-OHP) on inflammation in THP-1 monocytes stimulated with LPS was analyzed.

Figure 9:
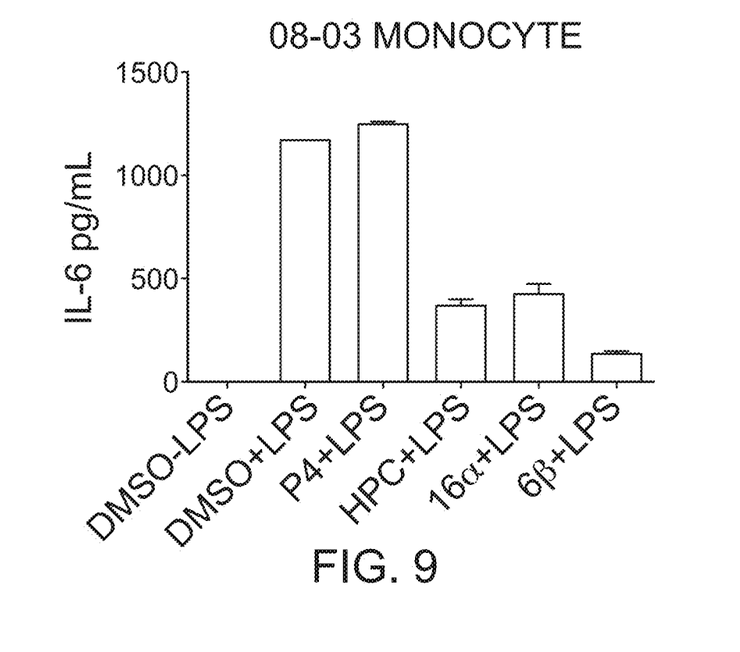
FIG. 9 is a graph depicting the effect of progesterone and progesterone metabolites (16αOHP and 6β-OHP) on inflammation in THP-1 monocytes stimulated with LPS. Monocytes pretreated with progesterone demonstrated a similar inflammatory response (IL-6) to the positive control. However, pre-treatment with progesterone metabolites 16αOHP and 6β-OHP significantly decreased IL-6 production.

As shown in FIG. 9, monocytes pretreated with progesterone demonstrated a similar inflammatory response (IL-6) to the positive control. However, pretreatment with progesterone metabolites 16αOHP and 6β-OHP significantly decreased IL-6 production.

These results demonstrated a consistent theme of modulation of inflammation by 6β-OHP and 16αOHP, often differing from the effect of the parent molecule progesterone. Both metabolites appear to mitigate LPS-induced inflammation in monocytes, while only 16αOHP retained this effect in UtSMC. In monocytes, it is believed that the metabolites have a post-transcriptional effect since NF-κB translocation appears unaltered. Both metabolites, but particularly 6β-OHP, appeared to hinder differentiation of monocytes to tissue macrophages and prevented the changes in cell surface marker expression seen with progesterone. It is further believed that 6β-OHP and 16αOHP may also affect TNF-α induced inflammation in monocytes/macrophages. Future experiments will be targeted to further characterize the effects of the metabolites and elucidate their mechanism of action.

What is claimed is:

1. A method of mitigating inflammation in a subject in need thereof, the method comprising administering a progesterone metabolite to the subject, wherein the progesterone metabolite is selected from the group consisting of 6β-hydroxyprogesterone (6β-OHP), 16α-hydroxyprogesterone (16α-OHP), and combinations thereof.

2. The method of claim 1, wherein the inflammation is localized inflammation.

3. The method of claim 2, wherein the localized inflammation is selected inflammation of uterine smooth muscle cells.

4. The method of claim 2, wherein the localized inflammation is in tissue macrophages.

5. The method of claim 1, wherein inflammation is systemic inflammation.

* * * * *